(12) United States Patent
Flynn et al.

(10) Patent No.: US 6,509,309 B2
(45) Date of Patent: Jan. 21, 2003

(54) CLEANING COMPOSITION COMPRISING ALKOXY SUBSTITUTED PERFLUORO COMPOUNDS

(75) Inventors: Richard M. Flynn, Mahtomedi, MN (US); George G. I. Moore, Afton, MN (US); John G. Owens, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/096,713

(22) Filed: Mar. 12, 2002

(65) Prior Publication Data

US 2002/0169098 A1 Nov. 14, 2002

Related U.S. Application Data

(60) Division of application No. 09/867,169, filed on May 29, 2001, now Pat. No. 6,380,149, which is a division of application No. 09/268,236, filed on Mar. 15, 1999, now Pat. No. 6,291,417, which is a continuation-in-part of application No. 08/573,416, filed on Dec. 15, 1995, now Pat. No. 5,925,611, which is a continuation-in-part of application No. 08/375,812, filed on Jan. 20, 1995, now abandoned.

(51) Int. Cl.$^7$ ............................ C11D 7/30; C11D 3/24
(52) U.S. Cl. .................... 510/412; 510/201; 510/202; 510/204; 510/245; 510/405; 510/407; 134/40
(58) Field of Search .......................... 510/201, 202, 510/204, 245, 405, 407, 412; 134/40

(56) References Cited

U.S. PATENT DOCUMENTS

| | | | |
|---|---|---|---|
| 3,278,615 A | * 10/1966 | Larsen et al. | 260/652.5 |
| 3,453,333 A | 7/1969 | Litt et al. | 260/614 |
| 3,516,938 A | 6/1970 | Zisman et al. | 252/171 |
| 3,542,859 A | 11/1970 | Litt et al. | 260/514 |
| 3,549,711 A | 12/1970 | Merrill et al. | 260/614 |
| 3,854,871 A | 12/1974 | Eanzel | 8/142 |
| 3,879,297 A | 4/1975 | Languille et al. | 252/8 |
| 3,882,182 A | 5/1975 | Benninger et al. | 260/584 |
| 3,897,502 A | 7/1975 | Russell et al. | 260/614 F |
| 3,900,372 A | 8/1975 | Childs et al. | 204/81 |
| 3,903,012 A | 9/1975 | Brandreth | 252/194 |
| 3,957,672 A | 5/1976 | Zisman et al. | 252/171 |
| 3,962,460 A | 6/1976 | Croix et al. | 424/342 |
| 3,976,788 A | 8/1976 | Regan | 424/342 |
| 3,981,928 A | 9/1976 | Pavlik | 260/615 F |
| 4,461,322 A | 7/1984 | Mills | 138/31 |
| 4,559,154 A | 12/1985 | Powell | 252/69 |
| 4,566,981 A | 1/1986 | Howells | 252/8.8 |
| 4,961,321 A | 10/1990 | O'Neill et al. | 62/114 |
| 5,023,009 A | 6/1991 | Merchant | 252/171 |
| 5,023,010 A | 6/1991 | Merchant | 252/171 |
| 5,026,498 A | 6/1991 | Merchant | 252/171 |
| 5,040,609 A | 8/1991 | Dougherty, Jr. et al. | 169/45 |
| 5,084,190 A | 1/1992 | Fernandez | 252/8 |
| 5,089,152 A | 2/1992 | Flynn et al. | 252/194 |
| 5,091,104 A | 2/1992 | Van Der Puy | 252/171 |
| 5,098,595 A | 3/1992 | Merchant | 252/171 |
| 5,115,868 A | 5/1992 | Dougherty, Jr. et al. | 169/45 |
| 5,117,917 A | 6/1992 | Robin et al. | 169/46 |
| 5,124,053 A | 6/1992 | Iikubo et al. | 252/8 |
| 5,125,978 A | 6/1992 | Flynn et al. | 134/2 |
| 5,141,654 A | 8/1992 | Fernandez | 252/8 |
| 5,157,159 A | 10/1992 | Janulis et al. | 568/677 |
| 5,169,873 A | 12/1992 | Behme et al. | 521/114 |
| 5,250,200 A | 10/1993 | Sallet | 252/8 |
| 5,264,462 A | 11/1993 | Hodson et al. | 521/88 |

(List continued on next page.)

FOREIGN PATENT DOCUMENTS

| | | | |
|---|---|---|---|
| CA | 2115984 | 2/1994 | ............ C09K/5/04 |
| DE | 1 294 949 | 5/1969 | |
| DE | 1 302 054 | 2/1970 | |
| EP | 0 496 899 A1 | 8/1982 | ........... B01D/12/00 |
| EP | 0 450 855 A2 | 10/1991 | ............ C11D/7/50 |
| EP | 0 454 109 A1 | 10/1991 | ............ C11D/7/50 |
| EP | 0 465 037 A1 | 1/1992 | ............ G03G/11/00 |
| EP | 0 787 537 A1 | 8/1997 | ............ B08B/3/08 |
| FR | 1.506.638 | 11/1967 | |
| FR | 2 287 432 | 5/1976 | ........... C07C/43/12 |
| GB | 1 193 122 | 5/1970 | ........... C07C/43/02 |
| GB | 2 274 462 | 7/1994 | ............ C09K/5/04 |
| JP | 5-271692 | 10/1993 | |
| JP | 6-192154 | 7/1994 | ........... C07C/43/12 |
| JP | 6-293685 | 10/1994 | ........... C07C/43/12 |
| JP | 6-293686 | 10/1994 | ........... C07C/43/12 |
| JP | 7-25803 | 1/1995 | ........... C07C/43/12 |
| JP | 95-69641 | 3/1995 | |
| JP | 8-259995 | 10/1996 | ............ C11D/7/28 |
| JP | 10-18176 | 1/1998 | |
| SU | 1 427 780 | 9/1990 | .......... A61K/31/40 |
| WO | WO 92/22678 | 12/1992 | ........... C23G/5/024 |
| WO | WO 93/09272 | 5/1993 | ........... C23G/5/032 |
| WO | WO 93/11201 | 6/1993 | ............ C09K/5/04 |
| WO | WO 93/11280 | 6/1993 | ............ C23G/5/02 |
| WO | WO 93/24586 | 12/1993 | ............ C09K/5/04 |
| WO | WO 94/20588 | 9/1994 | ............ C09K/5/04 |
| WO | WO 94/26837 | 11/1994 | ............ C09K/5/04 |

OTHER PUBLICATIONS

* English Language Abstract.

Climate Change: The IPCC Scientific Assessment, Cambridge University Press (1990).

(List continued on next page.)

Primary Examiner—Charles Boyer
(74) Attorney, Agent, or Firm—Lisa M. Fagan

(57) ABSTRACT

A process for removing contaminants from the surface of a substrate comprises contacting the substrate with a cleaning composition comprising at least one mono-, di-, or trialkoxy-substituted perfluoroalkane, perfluorocycloalkane, perfluorocycloalkyl-containing perfluoroalkane, or perfluorocycloalkylene-containing perfluoroalkane compound, the compound optionally containing additional catenary heteroatoms. The compounds exhibit good solvency properties while being environmentally acceptable.

2 Claims, No Drawings

U.S. PATENT DOCUMENTS

| | | | |
|---|---|---|---|
| 5,268,122 A | 12/1993 | Rao et al. | 252/171 |
| 5,275,669 A | 1/1994 | Van Der Puy et al. | 134/42 |
| 5,298,083 A | 3/1994 | Van Der Puy et al. | 134/42 |
| 5,352,378 A | 10/1994 | Mathisen et al. | 252/54 |
| 5,382,704 A | 1/1995 | Krespan et al. | 568/683 |
| 5,393,438 A | 2/1995 | Fernandez | 252/8 |
| 5,444,102 A | 8/1995 | Nimitz et al. | 521/131 |
| 5,536,327 A | 7/1996 | Kaiser | 134/1 |
| 5,658,962 A | 8/1997 | Moore et al. | 521/114 |

OTHER PUBLICATIONS

Cooper et al., "Tropospheric Lifetimes of Potential CFC Replacements: Rate Coefficients for Reaction with the Hydroxyl Radical," Atmosphere Environment, vol. 26A, No. 7, pp. 1331–1334 (1992).

Ellis, "Cleaning and Contamination of Electronics Components and Assemblies," Electrochemical Publication Limited, Ayr, Scotland, pp. 182–194 (1986).

England, "Catalytic Conversion of Fluoroalkyl Alkyl Ethers to Carbonyl Compounds," J. Org. Chem. vol. 49, pp. 4007–4008 (1984).

Evans et al., Formation of Fluorinated Ethers in a Modified Halohydrin Reaction, J. Org. Chem., vol. 33, No. 5, pp. 1839–1844 (1968).

Fisher et al., "Model Calculations of the relative effects of CFCs and their replacements on global warming," Nature, vol. 344, pp. 513–516 (1990).

Kobler et al., "Eine einfache Synthese von Tetraalkylammoniumsalzen mit funktionellen Anionen," Justus Liebigs Ann, Chem. pp. 1937–1945 (1978).

NFPA (National Fire Protection Association) 2001 Standard on Clean Agent Fire Extinguishing Systems, Section A–3–4.2.2, 1994 Edition.

Tang, "Atmospheric Fate of Various Fluorocarbons," M.S. Thesis, Massachusetts Institute of Technology (1993).

Tapscott et al., Halon Options Technical Working Conference Proceedings (1994).

Wang et al., "Climate Sensitivity of a One–Dimensional Radiative–Convective Model with Cloud Feedback," American Meteorological Society, vol. 38, pp. 1167–1178 (1981).

Wang et al., "A Model Study of the Greenhouse Effects Due to Increasing Atmospheric $CH_4$, $N_2O$, $CF_2Cl_2$, and $CFCl_3$," J. Geophys. Res., vol. 90, No. D7, pp. 12971–12980 (1985).

Yamabe, "Development of CFC Alternatives for Solvent Use," International Conference on CFC and BFC (Halons), Shanghai, China, pp. 24–30, Aug. 7–10, 1994.

Yamashita et al., "Development of CFC Alternatives Containing Oxygen Atom," International Conference on CFC and BFC (Halons), Shanghai, China, pp. 55–58, Aug. 7–10, 1994.

Yamashita et al., "Prediction of the Thermodynamic Properties of Fluorinated Ethers," Abstracts of the $14^{th}$ International Symposium on Fluorine Chemistry, Yokohama, Japan, Abstract No. 2P29, p. 276.

Young et al., "The Preparation of Some Derivatives of Chlorofluoroacetic Acid," J. Am. Chem. Soc., vol. 71, pp. 2432–2433 (1949).

Zhang et al., "Reactions of Hydroxyl Radicals with Several Hydrofluorocarbons: The Temperature Dependencies of the Rate Constants for $CHF_2CF_2CH_2F$ (HFC–235ca), $CF_3CHFCHF_2$ (HFC–236ea), $CF_3CHFCF_3$ (HFC–227ea), and $CF_3CH_2CH_2CF_3$ (HFC–356ffa)," J. Phys. Chem. vol. 98, No. 16, pp. 4312–4315 (1994).

Zurer, "Looming Ban on Production of CFCs, Halons Spurs Switch to Substitutes," Chemical & Engineering News, pp. 12–18 (1993).

Wang et al., "Vapor pressures, liquid molar volumes, vapor non–idealities, and critical properties of some fluorinated ethers: $CF_3OCF_2OCF_3$, $CF_3OCF_2CF_2H$, c–$CF_3CF_2O$, $CF_3OCF_2H$, and $CF_3OCH_3$; and of $CCl_3F$ and $CF_2CHI$," J. Chem. Thermodynamics, vol. 23, pp. 699–710 (1991).

Malcolm, "Vaporizing Fire Extinguishing Agents," Engineer Research and Development Laboratories, Fort Belvoir, Virginia, Interim Report 1177, Aug. 18, 1950.

Misaki et al., "Development of a New Refrigerant," 1994 International CFC and Halon Alternatives Conference Washington, D.C., pp. 114–120, Oct. 24–26, 1994.

Schmoltner et al., "Rate Coefficients for Reactions of Several Hydrofluorocarbons with OH and O(1D) and Their Atomospheric Lifetimes," J. Phys. Chem. vol. 97, pp. 8976–8982 (1993).

SNAP Technical Background Document: Risk Screen on the Use of Substitutes for Class I Ozone–Depleting Substances: Fire Suppression and Explosion Protection, U.S. EPA (Mar., 1994).

Sneed et al., Comprehensive Inorganic Chemistry, vol. Six (The Alkali Metals), pp. 61–64, D. Van Nostrand Company, Inc., New York (1957).

Suga et al., "Properties of Fluorinated Ethers," Abstracts of the $14^{th}$ International Symposium on Fluorine Chemistry, Yokohama, Japan, Abstract No. 4B04, p. 78 (1994).

* cited by examiner

CLEANING COMPOSITION COMPRISING ALKOXY SUBSTITUTED PERFLUORO COMPOUNDS

CROSS REFERENCE TO RELATED APPLICATIONS

This application is a divisional of U.S. application Ser. No. 09/867,169, filed May 29, 2001, issued as U.S. Pat. No. 6,380,149, which is a divisional of U.S. application Ser. No. 09/268,236, filed Mar. 15, 1999, issued as U.S. Pat. No. 6,291,417 which is a continuation-in-part of U.S. application Ser. No. 08/573,416, filed Dec. 15, 1995, issued as U.S. Pat. No. 5,925,611, which was a continuation-in-part of U.S. application Ser. No. 08/375,812, filed Jan. 20, 1995, now abandoned.

FIELD OF THE INVENTION

This invention relates to cleaning compositions comprising at least one partially-fluorinated ether compound and to processes for removing contaminants from substrate surfaces using such compositions. In another aspect, this invention relates to certain novel partially-fluorinated ether compounds. In yet another aspect, this invention relates to coating compositions comprising at least one partially-fluorinated ether compound and to processes for depositing coatings on substrate surfaces using such compositions.

BACKGROUND OF THE INVENTION

Solvent cleaning applications where contaminated articles are immersed in (or washed with) solvent liquids and/or vapors are well-known. Applications involving one or more stages of immersion, rinsing, and/or drying are common. Solvents can be used at ambient temperature (often, accompanied by ultrasonic agitation) or at elevated temperatures up to the boiling point of the solvent.

A major concern in solvent cleaning is the tendency (especially where solvent is used at an elevated temperature) for solvent vapor loss from the cleaning system into the atmosphere. Although care is generally exercised to minimize such losses (e.g., through good equipment design and vapor recovery systems), most practical cleaning applications result in some loss of solvent vapor into the atmosphere.

Solvent cleaning processes have traditionally utilized chlorinated solvents (e.g., chlorofluorocarbons such as 1,1, 2-trichloro-1,2,2-trifluoroethane and chlorocarbons such as 1,1,1-trichloroethane) alone or in admixture with one or more cosolvents such as aliphatic alcohols or other low molecular weight, polar compounds. Such solvents were initially believed to be environmentally-benign, but have now been linked to ozone depletion. According to the Montreal Protocol and its attendant amendments, production and use of the solvents must be discontinued (see, e.g., P. S. Zurer, "Looming Ban on Production of CFCs, Halons Spurs Switch to Substitutes," Chemical & Engineering News, page 12, Nov. 15, 1993).

Thus, there has developed a need in the art for substitutes or replacements for the commonly-used cleaning solvents. Such substitutes should have a low ozone depletion potential, should have boiling ranges suitable for a variety of solvent cleaning applications, and should have the ability to dissolve both hydrocarbon-based and fluorocarbon-based soils. Preferably, substitutes will also be low in toxicity, have no flash points (as measured by ASTM D3278-89), have acceptable stability for use in cleaning applications, and have short atmospheric lifetimes and low global warming potentials.

Partially-fluorinated ethers have been suggested as chlorofluorocarbon alternatives (see, e.g., Yamashita et al., International Conference on CFC and BFC (Halons), Shanghai, China, Aug. 7–10, 1994, pages 55–58).

European Patent Publication No. 0 450 855 A2 (Imperial Chemical Industries PLC) describes the use of low molecular weight, fluorine-containing ethers of boiling point 20–120° C. in solvent cleaning applications.

International Patent Publication No. WO 93/11280 (Allied-Signal, Inc.) discloses a non-aqueous cleaning process which utilizes a fluorocarbon-based rinsing solvent.

U.S. Pat. No. 5,275,669 (Van Der Puy et al.) describes hydrofluorocarbon solvents useful for dissolving contaminants or removing contaminants from the surface of a substrate. The solvents have 4 to 7 carbon atoms and have a portion which is fluorocarbon, the remaining portion being hydrocarbon.

U.S. Pat. No. 3,453,333 (Litt et al.) discloses fluorinated ethers containing at least one halogen substituent other than fluorine and states that those ethers which are liquid can be used as solvents for high molecular weight resinous perhalogenated compounds such as solid polychlorotrifluoroethylene resins.

French Patent Publication No. 2,287,432 (Societe Nationale des Poudres et Explosifs) describes new partially-fluorinated ethers and a process for their preparation. The compounds are said to be useful as hypnotic and anesthetic agents; as monomers for preparing heat-stable, fire-resistant, or self-lubricant polymers; and in phyto-sanitary and phyto-pharmaceutical fields.

German Patent Publication No. 1,294,949 (Farbwerke Hoechst AG) describes a technique for the production of perfluoroalkyl-alkyl ethers, said to be useful as narcotics and as intermediates for the reparation of narcotics and polymers.

SUMMARY OF THE INVENTION

In one aspect, this invention provides a process for removing contaminants (e.g., hydrocarbons, fluorocarbons, or even water) from the surface of a substrate (e.g., metal, glass, ceramic, plastic, or fabric). The process comprises contacting the substrate with (or exposing the substrate to) a liquid-and/or vapor-phase cleaning composition comprising at least one mono-, di-, or trialkoxy-substituted perfluoroalkane, perfluorocycloalkane, perfluorocycloalkyl-containing perfluoroalkane, or perfluorocycloalkylene-containing perfluoroalkane compound. The compound can optionally contain additional catenary (i.e., in-chain) heteroatoms (e.g., oxygen or nitrogen) and preferably has a boiling point in the range of from about 25° C. to about 200° C.

The alkoxy-substituted compounds used in the process of the invention exhibit unexpectedly high stabilities in the presence of acids, bases, and oxidizing agents. In addition, in spite of their fluorine content, the compounds are surprisingly good solvents for hydrocarbons (as well as fluorocarbons). The compounds are low in toxicity and flammability, have ozone depletion potentials of zero, and have short atmospheric lifetimes and low global warming potentials relative to chlorofluorocarbons and many chlorofluorocarbon substitutes. Since the compounds exhibit good solvency properties while being environmentally acceptable, they satisfy the need in the art for substitutes or replacements for the commonly-used cleaning solvents which have been linked to the destruction of the earth's ozone layer.

In other aspects, this invention also provides certain novel mono-, di-, and trialkoxy-substituted perfluorocompounds; a cleaning composition; a coating composition; and a process for depositing coatings (e.g., coatings of lubricant) on substrate surfaces.

DETAILED DESCRIPTION OF THE INVENTION

Compounds which can be utilized in the processes of the invention are mono-, di-, or trialkoxy-substituted perfluoroalkane, perfluorocycloalkane, perfluorocycloalkyl-containing perfluoroalkane, and perfluorocycloalkylene-containing perfluoroalkane compounds. The compounds include those which contain additional catenary heteroatoms (as well as those which do not) and can be utilized alone, in combination with one another, or in combination with other common cleaning solvents (e.g., alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, and hydrofluorocarbons). The compounds can be solids or liquids under ambient conditions of temperature and pressure, but are generally utilized for cleaning in either the liquid or the vapor state (or both). Thus, normally solid compounds can be utilized after tranformation to liquid and/or vapor through melting, sublimation, or dissolution in liquid co-solvent.

A class of useful alkoxy-substituted perfluorocompounds is that which can be represented by the following general formula (I):

$$R_f-(O-R_h)_x \qquad (I)$$

wherein x is an integer of 1 to 3; when x is 1, $R_f$ is selected from the group consisting of linear or branched perfluoroalkyl groups having from 2 to about 15, carbon atoms, perfluorocycloalkyl-containing perfluoroalkyl groups having from 5 to about 15 carbon atoms, and perfluorocycloalkyl groups having from 3 to about 12 carbon atoms; when x is 2, $R_f$ is selected from the group consisting of linear or branched perfluoroalkanediyl groups or perfluoroalkylidene groups having from 2 to about 15 carbon atoms, perfluorocycloalkyl- or perfluorocycloalkylene-containing perfluoroalkanediyl or perfluoroalkylidene groups having from 6 to about 15 carbon atoms, and perfluorocycloalkanediyl groups or perfluorocycloalkylidene groups having from 3 to about 12 carbon atoms; when x is 3, $R_f$ is selected from the group consisting of linear or branched perfluoroalkanetriyl groups having from 2 to about 15 carbon atoms, perfluorocycloalkyl- or perfluorocycloalkylene-containing perfluoroalkanetriyl groups having from 6 to about 15 carbon atoms, and perfluorocycloalkanetriyl groups having from 3 to about 12 carbon atoms; each $R_h$ is independently selected from the group consisting of linear or branched alkyl groups having from 1 to about 8 carbon atoms, cycloalkyl-containing alkyl groups having from 4 to about 8 carbon atoms, and cycloalkyl groups having from 3 to about 8 carbon atoms; wherein either or both of the groups $R_f$ and $R_h$ can contain (optionally contain) one or more catenary heteroatoms; and wherein the sum of the number of carbon atoms in $R_f$ and the number of carbon atoms in $R_h$ is greater than or equal to 4. The perfluorocycloalkyl and perfluorocycloalkylene groups contained within the perfluoroalkyl, perfluoroalkanediyl, perfluoroalkylidene and perfluoroalkanetriyl groups can optionally (and independently) be substituted with, e.g., one or more perfluoroalkyl groups having from 1 to about 4 carbon atoms.

Preferably, x is 1; $R_f$ is as defined above; $R_h$ is an alkyl group having from 1 to about 6 carbon atoms; $R_f$ but not $R_h$ can contain one or more catenary heteroatoms; and the sum of the number of carbon atoms in $R_f$ and the number of carbon atoms in $R_h$ is greater than or equal to 4. Most preferably, x is 1; $R_f$ is selected from the group consisting of linear or branched perfluoroalkyl groups having from 3 to about 6 carbon atoms, perfluorocycloalkyl-containing perfluoroalkyl or perfluoroalkylidene groups having from 5 to about 8 carbon atoms, and perfluorocycloalkyl groups having from 5 to about 6 carbon atoms; $R_h$ is an alkyl group having from 1 to about 3 carbon atoms; $R_f$ but not $R_h$ can contain one or more catenary heteroatoms; and the sum of the number of carbon atoms in $R_f$ and the number of carbon atoms in $R_h$ is greater than or equal to 4. The perfluorocycloalkyl and perfluorocycloalkylene groups contained within the perfluoroalkyl, perfluoroalkanediyl, perfluoroalkylidene and perfluoroalkanetriyl groups can optionally (and independently) be substituted with, e.g., one or more perfluoromethyl groups. These compounds are preferred due to their ease of preparation and their performance characteristics.

Representative examples of alkoxy-substituted perfluorocompounds suitable for use in the processes of the invention include the following compounds:

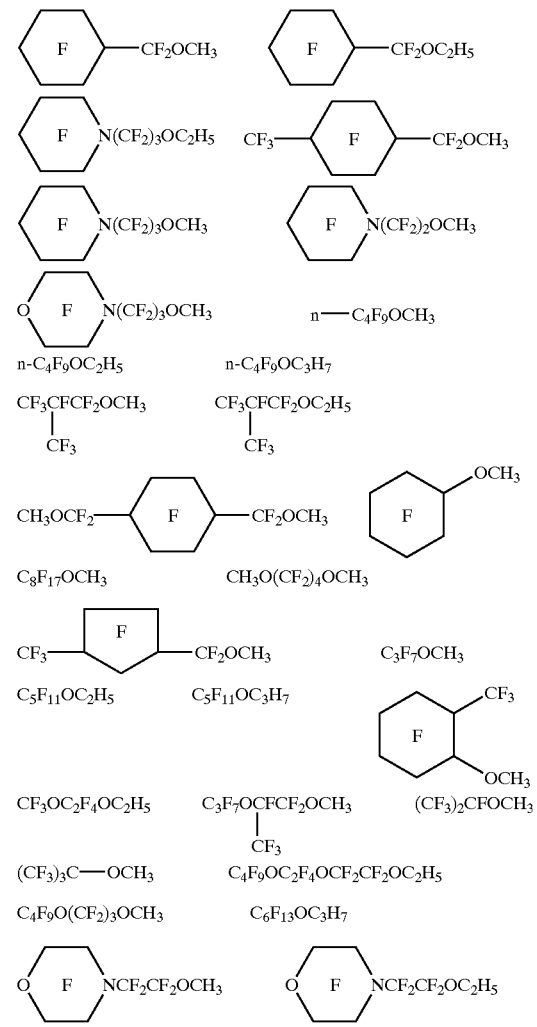

(C₂F₅)₂NCF₂CF₂OCH₃    (C₂F₅)₂NC₃F₆OCH₃

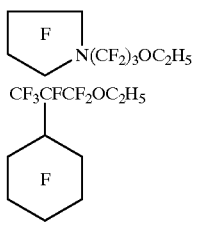

CF₃CFCF₂OC₂H₅

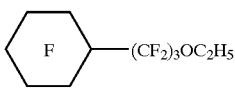

C₃F₇CF(OC₂H₅)CF(CF₃)₂, C₂F₅CF(OC₂H₅)CF(CF₃)₂, C₂F₅CF(OCH₃)CF(CF₃)₂, CF₃CF(OCH₃)CF(CF₃)₂, 1,1-dimethoxyperfluorocyclohexane, and mixtures thereof, where cyclic structures having an interior "F" are perfluorinated.

A novel subclass of the alkoxy-substituted perfluorocompounds is that which can be represented by the following general formula (II):

$$R_f^1-N(R_f^2)-C_yF_{2y}-O-R_h \quad (II)$$

wherein $R_f^1$ and $R_f^2$ are both substituted or unsubstituted perfluoroalkyl groups having from 1 to about 6 carbon atoms or are both substituted or unsubstituted perfluoroalkylene groups having from 2 to about 4 carbon atoms, the perfluoroalkylene groups being bonded to one another to form a ring; y is an integer of 1 to about 8; $C_yF_{2y}$ can be linear or branched; and $R_h$ is selected from the group consisting of linear or branched alkyl groups having from 1 to about 8 carbon atoms, cycloalkyl-containing alkyl groups having from 4 to about 8 carbon atoms, and cycloalkyl groups having from 3 to about 8 carbon atoms; wherein the groups $R_f^1$, $R_f^2$, and $R_h$ can optionally (and independently) contain one or more catenary heteroatoms.

Preferably, the perfluoroalkyl groups have from 1 to about 3 carbon atoms, the perfluoroalkylene groups have from 2 to about 3 carbon atoms; y is an integer of 1 to about 3; $R_h$ is selected from the group consisting of linear or branched alkyl groups having from 1 to about 6 carbon atoms; and $R_f^1$ and $R_f^2$ but not $R_h$ can independently contain one or more catenary heteroatoms. These compounds are preferred due to their ease of preparation and their performance characteristics.

Representative examples of novel compounds according to Formula II above include the following compounds:

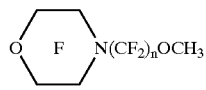
n = 1–4

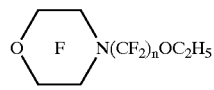
n = 1–4

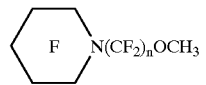
n = 1–4

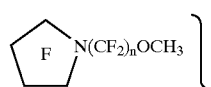
n = 1–4

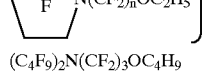
n = 1–4

(C₄F₉)₂N(CF₂)₃OC₄H₉    (C₄F₉)₂N(CF₂)₃OCH₃

(C₂F₅)₂N(CF₂)₆OCH₃

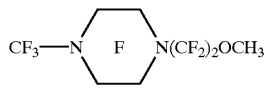

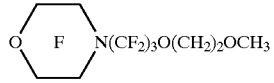

(CF₃)₂N(CF₂)₃OCH₃

(CF₃)₂N(CF₂)₂OC₂H₅    (C₂F₅)₂NCF₂CF₂OCH₃

C₂F₅NCF₂CF₂CF₂OC₂H₅    (C₃F₇)₂NCF₂CF₂CF₂OCH₃
   |
   CF₃

(C₃F₇)₂NCF₂CF₂CF₂OC₂H₅    (C₃F₇)₂NCF₂CF₂CF₂OC₃H₇

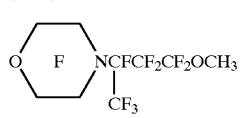

A second novel subclass of the alkoxy-substituted perfluorocompounds is that which can be represented by the following general formula (III):

$$R_f^3(CF_2OR_h)_{x'} \quad (III)$$

wherein $R_f^3$ is a substituted or unsubstituted perfluorocycloalkyl, perfluorocycloalkanediyl, or perfluorocycloalkanetriyl group having from 3 to about 12 carbon atoms; each $R_h$ is independently selected from the group consisting of linear or branched alkyl groups having from 1 to about 8 carbon atoms, cycloalkyl-containing alkyl-groups having from 4 to about 8 carbon atoms, and cycloalkyl groups having from 3 to about 8 carbon atoms; and x' is an integer of 1 to 3; wherein either or both of the groups $R_f^3$ and $R_h$ can contain (optionally contain) one or more catenary heteroatoms.

Preferably, $R_f^3$ has from 5 to about 6 carbon atoms; each $R_h$ is independently selected from the group consisting of linear or branched alkyl groups having from 1 to about 6 carbon atoms; x' is an integer of 1 or 2; and $R_f^3$ but not $R_h$ can contain one or more catenary heteroatoms. These compounds are preferred due to their ease of preparation and their performance characteristics.

Representative examples of novel compounds according to Formula III above include the following compounds:

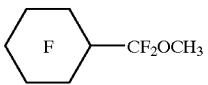

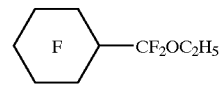

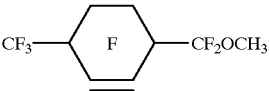

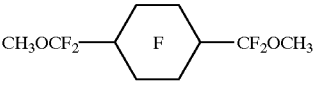

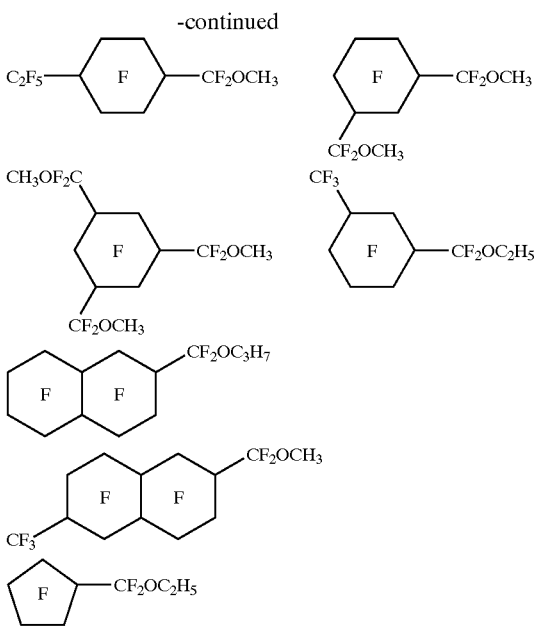

The alkoxy-substituted perfluorocompounds suitable for use in the process of the invention can be prepared by alkylation of perfluorinated alkoxides prepared by the reaction of the corresponding perfluorinated acyl fluoride or perfluorinated ketone with an anhydrous alkali metal fluoride (e.g., potassium fluoride or cesium fluoride) or anhydrous silver fluoride in an anhydrous polar, aprotic solvent. (See, e.g., the preparative methods described in French Patent Publication No. 2,287,432 and German Patent Publication No. 1,294,949, supra.) Alternatively, a fluorinated tertiary alcohol can be allowed to react with a base, e.g., potassium hydroxide or sodium hydride, to produce a perfluorinated tertiary alkoxide which can then be alkylated by reaction with alkylating agent.

Suitable alkylating agents for use in the preparation include dialkyl sulfates (e.g., dimethyl sulfate), alkyl halides (e.g., methyl iodide), alkyl p-toluenesulfonates (e.g., methyl p-toluenesulfonate), alkyl perfluoroalkanesulfonates (e.g., methyl perfluoromethanesulfonate), and the like. Suitable polar, aprotic solvents include acyclic ethers such as diethyl ether, ethylene glycol dimethyl ether, and diethylene glycol dimethyl ether; carboxylic acid esters such as methyl formate, ethyl formate, methyl acetate, diethyl carbonate, propylene carbonate, and ethylene carbonate; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof.

Perfluorinated acyl fluorides (for use in preparing the alkoxy-substituted perfluorocompounds) can be prepared by electrochemical fluorination (ECF) of the corresponding hydrocarbon carboxylic acid (or a derivative thereof), using either anhydrous hydrogen fluoride (Simons ECF) or KF.2HF (Phillips ECF) as the electrolyte. Perfluorinated acyl fluorides and perfluorinated ketones can also be prepared by dissociation of perfluorinated carboxylic acid esters (which can be prepared from the corresponding hydrocarbon or partially-fluorinated carboxylic acid esters by direct fluorination with fluorine gas). Dissociation can be achieved by contacting the perfluorinated ester with a source of fluoride ion under reacting conditions (see the method described in U.S. Pat. No. 3,900,372 (Childs), the description of which is incorporated herein by reference) or by combining the ester with at least one initiating reagent selected from the group consisting of gaseous, non-hydroxylic nucleophiles; liquid, non-hydroxylic nucleophiles; and mixtures of at least one non-hydroxylic nucleophile (gaseous, liquid, or solid) and at least one solvent which is inert to acylating agents.

Initiating reagents which can be employed in the dissociation are those gaseous or liquid, non-hydroxylic nucleophiles and mixtures of gaseous, liquid, or solid, non-hydroxylic nucleophile(s) and solvent (hereinafter termed "solvent mixtures") which are capable of nucleophilic reaction with perfluorinated esters. The presence of small amounts of hydroxylic nucleophiles can be tolerated. Suitable gaseous or liquid, non-hydroxylic nucleophiles include dialkylamines, trialkylamines, carboxamides, alkyl sulfoxides, amine oxides, oxazolidones, pyridines, and the like, and mixtures thereof. Suitable non-hydroxylic nucleophiles for use in solvent mixtures include such gaseous or liquid, non-hydroxylic nucleophiles, as well as solid, non-hydroxylic nucleophiles, e.g., fluoride, cyanide, cyanate, iodide, chloride, bromide, acetate, mercaptide, alkoxide, thiocyanate, azide, trimethylsilyl difluoride, bisulfite, and bifluoride anions, which can be utilized in the form of alkali metal, ammonium, alkyl-substituted ammonium (mono-, di-, tri-, or tetra-substituted), or quaternary phosphonium salts, and mixtures thereof. Such salts are in general commercially available but, if desired, can be prepared by known methods, e.g., those described by M. C. Sneed and R. C. Brasted in *Comprehensive Inorganic Chemistry*, Volume Six (The Alkali Metals), pages 61–64, D. Van Nostrand Company, Inc., New York (1957), and by H. Kobler et al. in Justus Liebigs Ann. Chem. 1978, 1937. 1,4-diazabicyclo [2.2.2]octane and the like are also suitable solid nucleophiles.

The cleaning process of the invention can be carried out by contacting a contaminated substrate with a cleaning composition comprising at least one of the above-described alkoxy-substituted perfluorocompounds. The perfluorocompounds can be utilized alone or in admixture with each other or with other commonly-used cleaning solvents, e.g., alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, and mixtures thereof. Such co-solvents can be chosen to modify or enhance the solvency properties of a cleaning composition for a particular use and can be utilized in ratios (of co-solvent to perfluorocompound(s)) such that the resulting composition has no flash point. Preferably, the perfluorocompound(s) constitute at least about 30 weight percent of the composition (more preferably, greater than about 50 weight percent, i.e., a major amount; most preferably, at least about 60 weight percent), based upon the sum of the weights of the perfluorocompound(s) and the co-solvent(s). The perfluorocompound(s) used in the composition preferably have boiling points in the range of from about 25° C. to about 200° C., more preferably from about 25° C. to about 125° C. If desirable for a particular application, the cleaning composition can further contain one or more dissolved or dispersed gaseous, liquid, or solid additives (for example, carbon dioxide gas, surfactants, stabilizers, antioxidants, or activated carbon).

The cleaning composition can be used in either the gaseous or the liquid state (or both), and any of the known techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182–94 (1986).

Both organic and inorganic substrates can be cleaned by the process of the invention. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, and blends thereof; fabrics comprising a blend of natural and synthetic fibers; and composites of the foregoing materials. The process is especially useful in the precision cleaning of electronic components (e.g., circuit boards), optical or magnetic media, and medical devices.

The cleaning process of the invention can be used to dissolve or remove most contaminants from the surface of a substrate. For example, materials such as light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; and other contaminants encountered in precision, electronic, metal, and medical device cleaning can be removed. The process is particularly useful for the removal of hydrocarbon contaminants (especially, light hydrocarbon oils), fluorocarbon contaminants, particulates, and water (as described in the next paragraph).

To displace or remove water from substrate surfaces, the cleaning process of the invention can be carried out as described in U.S. Pat. No. 5,125,978 (Flynn et al.) by contacting the surface of an article with a liquid cleaning composition which preferably contains a non-ionic fluoroaliphatic surface active agent. (Although non-ionic fluoroaliphatic surface active agents or surfactants are preferred, other surfactants that are sufficiently soluble or dispersible in the alkoxy-substituted perfluorocompound-containing cleaning composition can be utilized, if desired.) The wet article is immersed in the liquid composition and agitated therein, the displaced water is separated from the liquid composition, and the resulting Water-free article is removed from the liquid composition. Further description of the process and the articles which can be treated are found in said U.S. Pat. No. 5,125,978, which description is incorporated herein by reference. The process can also be carried out as described in U.S. Pat. No. 3,903,012 (Brandreth), the description of which is also incorporated herein.

This invention also provides a cleaning composition comprising (a) a major amount (greater than about 50 weight percent; preferably, at least about 60 weight percent) of at least one mono-, di-, or trialkoxy-substituted perfluoroalkane, perfluorocycloalkane, perfluorocycloalkyl-containing perfluoroalkane, or perfluorocycloalkylene-containing perfluoroalkane compound, the compound optionally containing additional catenary heteroatoms; and (b) a minor amount (less than about 50 weight percent; preferably, less than about 40 weight percent) of at least one co-solvent; said weight percents being based upon the sum of the weights of the perfluorocompound(s) (component (a) of the cleaning composition) and the co-solvent(s) (component (b) of the cleaning composition). Preferably, the co-solvent is selected from the group consisting of alcohols, ethers, alkanes, alkenes, haloalkenes, perfluorocarbons, perfluorinated tertiary amines, perfluoroethers, cycloalkanes, esters, ketones, aromatics, haloaromatics, siloxanes, hydrochlorocarbons, hydrochlorofluorocarbons, hydrofluorocarbons, and mixtures thereof(more preferably, alcohols, alkanes, alkenes, haloalkenes, cycloalkanes, esters, aromatics, haloaromatics, hydrochlorocarbons, hydrofluorocarbons, and mixtures thereof; most preferably, alcohols, alkanes, alkenes, haloalkenes, cycloalkanes, esters, aromatics, haloaromatics, and mixtures thereof).

Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, and mixtures thereof.

The above-described alkoxy-substituted perfluorocompounds can be useful not only in cleaning but also in coating deposition, where the perfluorocompound functions as a carrier for a coating material to enable deposition of the material on the surface of a substrate. The invention thus also provides a coating composition and a process for depositing a coating on a substrate surface using the composition. The process comprises the step of applying to at least a portion of at least one surface of a substrate a coating of a liquid coating composition comprising (a) a solvent composition comprising at least one mono-, di-, or trialkoxy-substituted perfluoroalkane, perfluorocycloalkane, perfluorocycloalkyl-containing perfluoroalkane, or perfluorocycloalkylene-containing perfluoroalkane compound, the compound optionally containing additional catenary heteroatoms; and (b) at least one coating material which is soluble or dispersible in the solvent composition. The solvent composition can further comprise one or more co-dispersants or co-solvents (as defined supra, preferably those having boiling points below about 125° C.) and/or one or more additives (e.g., surfactants, coloring agents, stabilizers, anti-oxidants, flame retardants, and the like).

Preferably, the process further comprises the step of removing the solvent composition from the coating by, e.g., allowing evaporation (which can be aided by the application of, e.g., heat or vacuum).

Coating materials which can be deposited by the process include pigments, lubricants, stabilizers, adhesives, antioxidants, dyes, polymers, pharmaceuticals, release agents, inorganic oxides, and the like, and combinations thereof. Preferred materials include perfluoropolyether, hydrocarbon, and silicone lubricants; amorphous copolymers of tetrafluoroethylene; polytetrafluoroethylene; and combinations thereof. Representative examples of materials suitable for use in the process include titanium dioxide, iron oxides, magnesium oxide, perfluoropolyethers, polysiloxanes, stearic acid, acrylic adhesives, polytetrafluoroethylene, amorphous copolymers of tetrafluoroethylene, and combinations thereof. Any of the substrates described above (for cleaning applications) can be coated via the process of the invention. The process can be particularly useful for coating magnetic hard disks or electrical connectors with perfluoropolyether lubricants or medical devices with silicone lubricants.

To form a coating composition, the components of the composition (i.e., the alkoxy-substituted perfluorocompound(s), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating, but the coating material(s) preferably constitute from about 0.1 to about 10 weight percent of the coating composition for most coating applications.

The deposition process of the invention can be carried out by applying the coating composition to a substrate by any conventional technique. For example, the composition can be brushed or sprayed (e.g., as an aerosol) onto the substrate, or the substrate can be spin-coated. Preferably, the substrate is coated by immersion in the composition. Immersion can be carried out at any suitable temperature and can be maintained for any convenient length of time. If the substrate is a tubing, such as a catheter, and it is desired to ensure that the composition coats the lumen wall, it may be advantageous to draw the composition into the lumen by the application of reduced pressure.

After a coating is applied to a substrate, the solvent composition can be removed from the coating by evaporation. If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Objects and advantages of this invention are further illustrated by the following examples, but the particular materials and amounts thereof recited in these examples, as well as other conditions and details, should not be construed to unduly limit this invention.

EXAMPLES

The environmental impact of the alkoxy-substituted perfluorocompounds used in the processes and compositions of the invention was assessed by determination of the atmospheric lifetime and the global warming potential (GWP) of certain compounds, as described below:

Atmospheric Lifetime

The atmospheric lifetime ($t_{sample}$) of various sample compounds was calculated by the technique described in Y. Tang, *Atmospheric Fate of Various Fluorocarbons*, M. S. Thesis, Massachusetts Institute of Technology (1993). According to this technique, an ultraviolet (UV) gas cell was charged with a sample compound, a reference compound (either $CH_4$ or $CH_3Cl$), ozone, and water vapor. Hydroxyl radicals were then generated by photolytic decomposition of the ozone in the presence of the water vapor and an inert buffer gas, i.e., helium. As the sample compounds and reference compounds reacted with the hydroxyl radicals in the gas phase, their concentrations were measured by Fourier transform infrared spectroscopy (FTIR). The rate constant for reaction of the sample compound ($k_{sample}$) with hydroxyl radical was measured relative to the rate constant for a reference compound ($k_{ref}$), and the atmospheric lifetime was then calculated using the following formula (where $\tau_{CH4}$ and $k_{CH4}$ are known values of 12 years and $6.5 \times 10^{-15}$ cm$^3$/molecule-sec, respectively):

$$\tau_{sample} = \frac{\tau_{CH4}}{\left(\frac{k_{sample}}{k_{ref}}\right)\left(\frac{k_{ref}}{k_{CH4}}\right)}$$

The rate constant for each sample compound was measured (using $CH_4$ as the reference compound and again using $CH_3Cl$) at 298K, and the atmospheric lifetime values were calculated and then averaged. The results are shown in Table A under the heading "Atmospheric Lifetime." For comparative purposes, the atmospheric lifetime for several hydrofluorocarbons is also shown in Table A.

Atmospheric lifetime was also estimated from a correlation developed between the highest occupied molecular orbital (HOMO) energy and the known atmospheric lifetimes of hydrofluorocarbons and hydrofluorocarbon ethers, in a manner similar to that described by Cooper et al. in Atmos. Environ. 26A, 7, 1331 (1992). The correlation differed from that found in Cooper et al. in the following respects: the correlation was developed using a larger data set; lifetimes for the correlations were determined by relative hydroxyl reactivity of the sample to $CH_3CCl_3$ at 277K, as described by Zhang et al. in J. Phys. Chem. 98(16), 4312 (1994); HOMO energy was calculated using MOPAC/PM3, a semi-empirical molecular orbital package; and the number of hydrogen atoms present in the sample was included in the correlation. The results are reported in Table A under the heading "Estimated Atmospheric Lifetime."

Global Warming Potential

Global warming potential (GWP) was determined for the various sample compounds using the above-described calculated values for atmospheric lifetime and experimentally determined infrared absorbance data integrated over the spectral region of interest, typically 500 to 2500 cm$^{-1}$. The calculations were based on the definition of GWP set forth by the Intergovernmental Panel in Climate Change in *Climate Change: The IPCC Scientific Assessment*, Cambridge University Press (1990). According to the Panel, GWP is the integrated potential warming due to the release of 1 kilogram of sample compound relative to the warming due to 1 kilogram of $CO_2$ over a specified integration time horizon (ITH) using the following equation:

$$GWP_{sample} = \frac{\int_0^{ITH} \Delta T_X C_{Ox} e^{-t/\tau x} dt}{\int_0^{ITH} \Delta T_{CO_2} C_{co_2} dt}$$

where ΔT is the calculated change in temperature at the earth's surface due to the presence of a particular compound in the atmosphere [calculated using a spreadsheet model (using parameters described by Fisher et al. in Nature 344, 513 (1990)) derived from Atmospheric and Environmental Research, Inc.'s more complete one-dimensional radiative-convective model (described by Wang et al. in J. Atmos. Sci. 38, 1167 (1981) and J. Geophys. Res. 90, 12971 (1985)], C is the atmospheric concentration of the compound, τ is the atmospheric lifetime of the compound (the calculated value described above), and x designates the compound of interest. Upon integration, the formula is as follows:

$$GWP_{sample} = \frac{\Delta T_X C_{Ox} \tau_X [1 - e^{-ITH/\tau x}]}{\Delta T_{CO_2}(1.3 \times 10^{-10})[A_1 \tau_1 (1 - e^{-ITH/\tau 1}) + A_2 \tau_2 (1 - e^{-ITH/\tau 2}) + A_3 \tau_3 (1 - e^{-ITH/\tau 3})]}$$

where $A_1=0.30036$, $A_2=0.34278$, $A_3=0.35686$, $\tau_1=6.993$, $\tau_2=71.108$, and $\tau_3=815.73$ in the Siegenthaler (1983) coupled ocean-atmosphere $CO_2$ model. The results of the calculations are shown in Table A below.

TABLE A

| Compound | Estimated Atmospheric Lifetime (years) | Atmospheric Lifetime (years) | Global Warming Potential (100 year ITH) |
|---|---|---|---|
| $CF_3$—$CH_3$ | 62.2 | | |
| $CF_3$—O—$CH_3$ | 1.6 | | |
| $C_2F_5$—$CH_3$ | 12.6 | | |
| $C_2F_5$—O—$CH_3$ | 1.6 | | |
| $C_3F_7$—$CH_3$ | 9.6 | | |
| $C_3F_7$—O—$CH_3$ | 1.9 | | |
| $C_4F_9$—$CH_3$ | 7.0 | | |
| $C_4F_9$—O—$CH_3$ | 1.9 | 5.5 | 330 |
| $C_4F_9$—$C_2H_5$ | 2.0 | | |
| $C_4F_9$—O—$C_2H_5$ | 0.5 | 1.2 | 70 |
| $C_5F_{11}OCH_3$ | 4.3 | | |
| $CF_3CF(OCH_3)CF(CF_3)_2$ | 4–5 | | |
| $C_5F_{11}OC_2H_5$ | ~1 | | |
| c—$C_6F_{11}$—$CH_3$ | 13.7 | | |
| c—$C_6F_{11}$—O—$CH_3$ | 1.8 | 3.8 | 170 |
| $C_2F_5CF(OCH_3)CF(CF_3)_2$ | 4–5 | | |
| $CF_3CFHCFHCF_2CF_3$ | 23* | | 1000 |

A. M. Schmoltner et al., J. Phys. Chem. 97, 8976 (1993)

As can be seen in Table A, each of the various alkoxy-substituted perfluorocompounds unexpectedly has a lower atmospheric lifetime than the corresponding hydrofluorocarbon, i.e., the hydrofluorocarbon having the same carbon number. The alkoxy-substituted perfluorocompounds are thus more environmentally acceptable than the hydrofluorocarbons (which have previously been proposed as chlorofluorocarbon replacements).

The chemical stability of the alkoxy-substituted perfluorocompounds used in the processes and compositions of the invention was also evaluated to determine their suitability for use in cleaning and coating applications. In these tests, a compound was contacted with a chemical agent such as aqueous sodium acetate, aqueous KOH, concentrated sulfuric acid, or potassium permanganate in acetone to determine the stability of the compound to base, acid, or oxidant, as described below:

Stability in the Presence of Base

To assess hydrolytic stability, a ten gram sample of alkoxy-substituted perfluorocompound was combined with 10 g of 0.1 M NaOAc and sealed in a 2.54 cm (internal diameter) by 9.84 cm Monel™ 400 alloy (66% nickel, 31.5% copper, and 1.2% iron and several minor components) tube (available from Paar Instrument Co. of Moline, Illinois as Part Number 4713 cm). The tube was heated at 110° C. in a forced air convection oven for 16 hours. After cooling to room temperature, a 1 mL sample of the tube contents was diluted with 1 mL of total ionic strength adjustment buffer (TISAB, available from Orion Research, Inc., a mixture of 1,2-cyclohexylene dinitrilotetraacetic acid, deionized water, sodium acetate, sodium chloride, and acetic acid). The concentration of fluoride ion (resulting from any reaction of the perfluorocompound with the aqueous NaOAc) was measured using an Orion Model 720A Coulombmeter with a $F^{31}$ specific electrode which had been previously calibrated using 0.5 and 500 ppm $F^-$ solutions. Based on the measured fluoride ion concentration, the rate at which HF had been generated by reaction of the aqueous NaOAc with the perfluorocompound was calculated. The results are shown below in Table B and indicate that the alkoxy-substituted perfluorocompounds are much more stable to base than is the comparative compound.

TABLE B

| | $C_4F_9OCH_3$ | $C_4F_9OC_2H_5$ | c—$C_6F_{11}OCH_3$ | $CF_3CFHCFHCF_2CF_3$ |
|---|---|---|---|---|
| HF Generation Rate (μg/g/hr) | 0.67 | 0.22 | 0.33 | 42.9 |

To assess hydrolytic stability under more severely basic conditions, $C_4F_9OCH_3$ (125 g of 99.8% purity, 0.5 mole) was combined with potassium hydroxide (29.4 g, 0.45 mole, dissolved in 26.1 g water) in a 250 mL flask equipped with an overhead stirrer, a condenser, and a thermometer, and the resulting solution was refluxed at 58° C. for 19 hours. Water (50 mL) was added to the solution after refluxing, and the resulting product was distilled. The lower fluorochemical phase of the resulting distillate was separated from the upper phase and was washed with water (100 mL) to yield 121.3 g of recovered $C_4F_9OCH_3$, which was identical in purity and composition to the starting material (as shown by gas chromatography). The aqueous base solution remaining in the reaction flask was titrated with standard 1.0 N HCl to reveal that none of the KOH originally charged had been consumed, indicating that the perfluorocompound was stable in the presence of the base.

Stability in the Presence of Acid

To assess hydrolytic stability under acidic conditions, $C_4F_9OCH_3$ (15 g, 0.06 mole) was combined with sulfuric acid (10 g of 96% by weight, 0.097 mole) in a 50 mL flask containing a stir bar and fitted with a reflux condenser. The resulting mixture was stirred for 16 hours at room temperature, and then the resulting upper fluorochemical phase was separated from the resulting lower sulfuric acid phase. Gas-liquid chromatographic (GLC) analysis of the fluorochemical phase revealed the presence of only the starting perfluorocompound and no detectable amount of $C_3F_7CO_2CH_3$, the expected product of hydrolysis. This result (indicating that the perfluorocompound was stable in the presence of the acid) was surprising in view of the discussion by England in J. Org. Chem. 49, 4007 (1984), which states that "[f]luorine atoms attached to carbon which also bears an alkyl ether group are known to be labile to electrophilic reagents. They are readily hydrolyzed in concentrated sulfuric acid, thus providing a route to some esters of fluoroacids."

Stability in the Presence of Oxidant

To assess oxidative stability, potassium permanganate (20 g, 0.126 mole) was dissolved in acetone, and $C_4F_9OCH_3$ (500 g of 99.9% purity, 2.0 mole) was added to the resulting solution. The solution was refluxed for four hours, with no indication that the permanganate had been consumed (as evidenced by the absence of brown $MnO_2$). The refluxed solution was then distilled into a 500 mL Barrett trap filled with water. The lower fluorochemical phase of the resulting mixture was separated from the upper phase, was washed with four 1.5 L aliquots of water, and was dried by passage through a column of silica gel to yield 471 g of resulting product. Gas chromatographic analysis of the product revealed no evidence of degradation of the starting perfluorocompound, indicating that the compound was stable in the presence of the oxidant.

Flash Point Testing

The alkoxy-substituted perfluorocompounds $C_4F_9OCH_3$, $C_4F_9OC_2H_5$, and c-$C_6F_{11}OCH_3$ were tested for flash point by the standard method defined by ASTM D3278-89. Each compound was determined to have no flash point.

Examples 1–7 describe the preparation of novel alkoxy-substituted perfluorocompounds of the invention.

Example 1

Preparation of c-$C_6F_{11}CF_2OC_2H_5$

A one liter jacketed round bottom flask was equipped with a reflux condenser, an overhead stirrer, and an addition funnel. The flask was charged with anhydrous dimethyl formamide (300 g) and diethyl sulfate (239 g, 1.55 mole) under a flow of dry nitrogen gas. The resulting stirred solution was cooled to −20° C., and spray-dried potassium fluoride (Aldrich Chemical, which was further dried at 120° C., 67.5 g, 1.16 mole) was added. A mixture of perfluorocyclohexane carbonyl fluoride and isomers of perfluoro methylcyclopentane carbonyl fluoride (approximately 80% purity, 318 g, 0.77 mole) was then added to the resulting mixture over a period of 45 minutes. (Hereinafter, c-$C_6F_{11}$— refers to a mixture of the perfluorinated cyclohexyl and methyl cyclopentyl isomers.) The mixture was held at −20° C. for two hours and then allowed to come to ambient temperature while stirring overnight. The mixture was transferred to a two liter round bottom flask and was heated to 50° C. for one hour. One liter of water was added and the resulting mixture distilled. The lower fluorochemical phase of the resulting distillate was then separated from the upper phase and was washed once with water to afford 236 g of 61.9% purity c-$C_6F_{11}CF_2OC_2H_5$. The product was distilled to a purity of 99% (b.=128–134° C.). The product identity was confirmed by gas chromatography/ mass spectrometry (GCMS) and by $^1H$ and $^{19}F$ nuclear magnetic resonance spectroscopy (NMR).

Example 2

Preparation of c-$C_6F_{11}CF_2OCH_3$

A 500 mL round bottom flask was equipped with an overhead stirrer, a condenser, and an addition funnel, and was then charged with spray-dried potassium fluoride (Aldrich, which was further dried at 120° C., 39.8 g, 0.68 mole) and anhydrous dimethyl formamide (250 g). c-$C_6F_{11}COF$ (150 g of 70% purity, 0.32 mole) was added slowly to the resulting mixture at room temperature. An ice bath was then placed around the flask, and dimethyl sulfate (74.8 g, 0.59 mole) was added dropwise. The resulting mixture was held in the ice bath for five hours, followed by warming to ambient temperature with stirring overnight. Water (100 mL) was then added to the mixture, and the resulting product was distilled. The lower fluorochemical phase of the resulting distillate was separated from the upper aqueous phase to yield 143 g of c-$C_6F_{11}CF_2OCH_3$ of 63% purity. The products of several reactions were combined and distilled (b.=110–120° C.). The product identity was confirmed by GCMS and by $^1H$ and $^{19}F$ NMR.

Example 3

Preparation of 4-$CF_3$-c-$C_6F_{10}CF_2OCH_3$

A one liter round bottom flask was equipped with an overhead stirrer, a condenser, and an addition funnel and was then charged with spray-dried potassium fluoride (Aldrich, which was further dried at 120° C., 15.4 g, 0.26 mole), anhydrous cesium fluoride (6.5 g, 0.043 mole), and anhydrous dimethyl formamide (250 g). A mixture of perfluoro-4-methylcyclohexane carbonyl fluoride and perfluorodimethyl cyclopentane carbonyl fluorides (100 g of 72% purity, 0.189 mole) was then added to the resulting mixture, and the mixture was stirred at ambient temperature for four hours. Dimethyl sulfate (33.3 g, 0.264 mole) was then added to the stirred mixture, and the mixture was further stirred for 72 hours followed by addition of water (500 mL).

The mixture was worked up essentially as described in Example 1 to yield 67 g of a mixture of several components, which was subsequently distilled to give 26.5 g of 4-$CF_3$- c-$C_6F_{10}CF_2OCH_3$ (b.=118–137° C.) of 88% purity. The product identity was confirmed by GCMS and by $^1H$ and $^{19}F$ NMR, which showed the product to be about 60% of the trans-1,4 isomer and 15% of the cis-1,4 isomer. The product also contained several other isomers of $CF_3$-c-$C_6F_{10}CF_2OCH_3$, resulting from isomers of the perfluoromethylcyclohexane carbonyl fluoride which were present in the starting material.

Example 4

Preparation of

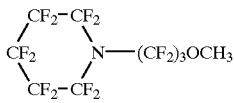

The title compound was prepared essentially as in Example 3 using anhydrous potassium fluoride (27 g, 0.46 mole), anhydrous dimethyl formamide (250 g), perfluoro-3-piperidinopropionyl fluoride (322 g of 40.4% purity, 0.32 mole), and dimethyl sulfate (52 g, 0.41 mole). 275 g of a product mixture of 38% purity was obtained, which was fractionally distilled to give a main fraction of the desired compound (b.=137–139° C., 91% purity). The product identity was confirmed by infrared spectroscopy (IR), GCMS, and $^1H$ and $^{19}F$ NMR.

Example 5

Preparation of

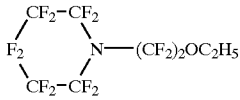

The title compound was prepared essentially as in Example 3 using anhydrous potassium fluoride (42 g, 0.72 mole), anhydrous dimethyl formamide (300 g), perfluoro-2-piperidinoacetyl fluoride (354 g of 47.2% purity, 0.46 mole), and diethyl sulfate (94 g, 0.61 mole). 349 g of a product mixture of 39% purity was obtained, which was fractionally distilled to give a main fraction of the desired compound (b.=135–137° C.). The product identity was confirmed by IR, GCMS, and $^1H$ and $^{19}F$ NMR.

Example 6

Preparation of

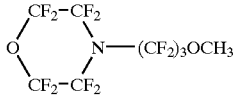

The title compound was prepared essentially as in Example 3 using anhydrous potassium fluoride (17.7 g, 0.30 mole), anhydrous dimethyl formamide (300 g), perfluoro-3-morpholinopropionyl fluoride (890 g of 8.6% purity, 0.2 mole), and dimethyl sulfate (37 g, 0.29 mole). 88 g of a product mixture of 57% purity was obtained, which was fractionally distilled to give a main fraction of the desired compound (b.p.=129° C., 90% purity). The product identity was confirmed by IR, GCMS, and $^1H$ and $^{19}F$ NMR.

Example 7

Preparation of $CH_3OCF_2$-c-$C_6F_{10}CF_2OCH_3$

The title compound was prepared essentially as in Example 3 using anhydrous potassium fluoride (6.62 g, 0.011 mole), anhydrous dimethyl formamide (200 g), FCO-c-$C_6F_{10}$COF (253 g of approximately 26% purity, 0.185 mole; the remainder of the material comprised a mixture of mono-functional, non-functional, and isomeric compounds), and dimethyl sulfate (14.4 g, 0.011 mole). 21 g of solid $CH_3OCF_2$-c-$C_6F_{10}CF_2OCH_3$ was obtained (product identity confirmed by IR and $^1H$ and $^{19}F$ NMR).

Examples 8–28 describe the use of alkoxy-substituted perfluorocompounds in various different cleaning applications according to the cleaning process of the invention.

A number of different alkoxy-substituted perfluorocompounds were prepared for use in cleaning, as described below:

Preparation of $C_4F_9OC_2H_5$

A 20 gallon Hastalloy C reactor, equipped with a stirrer and a cooling system, was charged with spray-dried potassium fluoride (7.0 kg, 120.3 mole). The reactor was sealed, and the pressure inside the reactor was reduced to less than 100 torr. Anhydrous dimethyl formamide (22.5 kg) was then added to the reactor, and the reactor was cooled to below 0° C. with constant agitation. Heptafluorobutyryl fluoride (22.5 kg of 58% purity, 60.6 mole) was added to the reactor contents. When the temperature of the reactor reached −20° C., diethyl sulfate (18.6 kg, 120.8 mole) was added to the reactor over a period of approximately two hours. The resulting mixture was then held for 16 hours with continued agitation, was raised to 50° C. for an additional four hours to facilitate complete reaction, and was cooled to 20° C. Then, volatile material (primarily perfluorooxacyclopentane present in the starting heptafluorobutyryl fluoride) was vented from the reactor over a three-hour period. The reactor was then resealed, and water (6.0 kg) was added slowly to the reactor. After the exothermic reaction of the water with unreacted perfluorobutyryl fluoride subsided, the reactor was cooled to 25° C., and the reactor contents were stirred for 30 minutes. The reactor pressure was carefully vented, and the lower organic phase of the resulting product was removed to afford 17.3 kg of material which was 73% $C_4F_9OC_2H_5$ (b.p.=75° C.). The product identity was confirmed by GCMS and by $^1H$ and $^{19}F$ NMR.

Preparation of $C_4F_9OCH_3$

The reaction was carried out in the same equipment and in a similar manner to the procedure of Example 7 above, but using the following materials: spray-dried potassium fluoride (6 kg, 103.1 mole), anhydrous dimethyl formamide (25.1 kg), perfluorobutyryl fluoride (58% purity, 25.1 kg, 67.3 mole), and dimethyl sulfate (12.0 kg, 95.1 mole). 22.6 kg of product was obtained, which was 63.2% $C_4F_9OCH_3$ (b.=58–60° C.). The product identity was confirmed by GCMS and by $^1H$ and $^{19}F$ NMR.

Preparation of c-$C_6F_{11}OCH_3$

A 500 ml, 3-necked round bottom flask equipped with an overhead stirrer, an addition funnel, and a condenser was charged with anhydrous cesium fluoride (27.4 g, 0.18 mole), anhydrous diethylene glycol dimethyl ether (258 g, hereinafter diglyme), and dimethyl sulfate (22.7 g, 0.18 mole). Perfluorocyclohexanone (50g, 0.18 mole) was then added dropwise to the resulting stirred mixture, and stirring was continued for 18 hours after the addition. Water (approximately 200 ml) was added to the resulting mixture, and the lower fluorochemical phase of the mixture was separated from the upper phase and washed once with saturated aqueous sodium chloride solution. Since the fluorochemical phase still contained about 12% diglyme, water was added to it, and the resulting product was azeotropically distilled to yield 32.8 g of c-$C_6F_{11}OCH_3$ (b.p.=100° C.), which was free of diglyme. The product identity was confirmed by IR, GCMS, and $^1H$ and $^{19}F$ NMR.

Preparation of $(CF_3)_2CFCF_2OCH_3$

The title compound was prepared essentially as in Example 1 using anhydrous potassium fluoride (31.9 g, 0.55 mole), anhydrous dimethyl formamide (186 g), perfluoroisobutryl fluoride (108 g of 99% purity, 0.5 mole), and dimethyl sulfate (81.9 g, 0.65 mole). The resulting mixture was held at −20° C. for 16 hours, was warmed to 40° C. for 3.5 hours, and was then distilled to yield 109 g of the title compound (83.6% purity by GLC; also containing 11.6% $(CF_3)_2CFCOF$). The reaction mixtures from several runs were combined and distilled (b.=60–61° C.).

Preparation of $(CF_3)_2CFCF_2OC_2H_5$

The title compound was prepared essentially as in Example 1 using anhydrous potassium fluoride (31.9 g, 0.55 mole), anhydrous dimethyl formamide (184 g), perfluoroisobutryl fluoride (112.3 g of 77% purity, 0.4 mole), and diethyl sulfate (100.1 g, 0.65 mole). The resulting mixture was worked up essentially as in Example 3 to yield 80 g of the title compound. The product identity was confirmed by IR, GCMS, and $^1H$ and $^{19}F$ NMR.

Preparation of $C_8F_{17}OCH_3$

The title compound was prepared essentially as in Example 3 using anhydrous potassium fluoride (6.62 g, 0.011 mole), anhydrous dimethyl formamide (800 g), $C_7F_{15}COF$ (456.7 g, 1.09 mole), and dimethyl sulfate (14.4 g, 0.011 mole). The resulting mixture was worked up essentially as in Example 3 to give 444 g of the title compound (99.7% purity, b.=142–144° C.). The product identity was confirmed by IR, GCMS, and $^1H$ and $^{19}F$ NMR.

Preparation of $C_2F_5CF(OCH_3)CF(CF_3)_2$

The title compound was prepared essentially as in Example 3 using anhydrous potassium fluoride (7.2 g, 0.123 mol), anhydrous diethylene glycol dimethyl ether (diglyme, 60 g), methyltrialkyl($C_8$–$C_{10}$)ammonium chloride (Adogen™ 464, available from Aldrich Chemical Company, 1.8 g; which can preferably be purified by addition of anhydrous diglyme, followed by vacuum distillation up to the boiling point of diglyme, to remove any low boiling components and some diglyme to give a final concentration of approximately 50% by weight of Adogen™ 464 in diglyme), $C_2F_5COCF(CF_3)_2$ (30 g, 0.095 mol, prepared by the reaction of pentafluoropropionyl fluoride with KF and hexafluoropropene), and dimethyl sulfate (15.5 g, 0.123 mol). The reaction mixture was stirred at room temperature for 72 hours. Approximately 100 mL of 10% aqueous potassium hydroxide was then added to the reaction mixture, and the resulting product was azeotropically distilled from the mixture. The lower phase of the resulting distillate was separated from the upper phase, was washed with water, and was distilled to give 26.7 g of product ether (boiling range 90–92° C.; >99% purity by gas-liquid chromatography (GLC)). The product identity was confirmed by GCMS and $^1H$ and $^{19}F$ NMR.

Preparation of $C_3F_7OCH_3$

A jacketed one liter round bottom flask was equipped with an overhead stirrer, a solid carbon dioxide/acetone condenser, and an addition funnel. The flask was charged with spray-dried potassium fluoride (85 g, 1.46 mol) and anhydrous diethylene glycol dimethyl ether (375 g) and was then cooled to about −20° C. using a recirculating refrigeration system. $C_2F_5COF$ (196 g, 1.18 mol) was added to the flask over a period of about one hour. The flask was then warmed to about 24° C., and dimethyl sulfate (184.3 g, 1.46 mol) was then added dropwise via the addition funnel over a 45 minute period. The resulting mixture was then stirred at room temperature overnight. Water (a total of 318 mL) was then added dropwise to the mixture. The mixture was transferred to a one liter round bottom flask, and the resulting product ether was azeotropically distilled. The lower product phase of the resulting distillate was separated from the upper aqueous phase, was washed once with cold water, and was subsequently distilled to give 180 g of product (b.p. 36° C.; >99.9% purity by GLC). The product identity was confirmed by GCMS and by $^1H$ and $^{19}F$ NMR.

Preparation of $CF_3CF(OCH_3)CF(CF_3)_2$

The title compound was prepared essentially as in Example 3 using anhydrous potassium fluoride (12.8 g, 0.22 mol), anhydrous diethylene glycol dimethyl ether (diglyme, 106 g), methyltrialkyl($C_8$–$C_{10}$)ammonium chloride (Adogen™ 464, available from Aldrich Chemical Company, 4 g), $CF_3COCF(CF_3)_2$ (53.2 g, 0.20 mol, prepared essentially by the procedure of Smith et al., J. Am. Chem. Soc., 84, 4285 (1962)), and dimethyl sulfate (33.9 g, 0.72 mol). Aqueous potassium hydroxide was added to the reaction mixture (approximately 25 g of 50% solution), followed by water (200 mL). The resulting crude product was azeotropically distilled from the reaction mixture. The lower phase of the resulting distillate was separated from the upper phase, was washed with water, was dried over anhydrous sodium sulfate, and was distilled (b.p. 82–83° C.; yield of 45 g). The product identity was confirmed by GCMS and by FTIR.

Preparation of $C_5F_{11}OCH_3$

The title compound was prepared essentially as in Example 3 using anhydrous potassium fluoride (32 g, 0.55 mol), anhydrous diethylene glycol dimethyl ether (diglyme, 375 g), methyltrialkyl($C_8$–$C_{10}$)ammonium chloride (Adogen™ 464, available from Aldrich Chemical Company, 12.5 g; which can preferably be purified by addition of anhydrous diglyme, followed by vacuum distillation up to the boiling point of diglyme, to remove any low boiling components and some diglyme to give a final concentration of approximately 50% by weight of Adogen™ 464 in diglyme), $C_4F_9COF$ (218 g of 60.7% purity, 0.5 mol), and dimethyl sulfate (69.3 g, 0.55 mol). The reaction mixture was stirred at room temperature overnight. Approximately 100 mL of 10% aqueous potassium hydroxide was then added to the mixture, and the resulting product was azeotropically distilled from the mixture. The lower phase of the resulting distillate was separated from the upper phase, was washed with water, was treated with aqueous potassium hydroxide solution (53 g of 50%), and was then refluxed for one hour. A second azeotropic distillation and water washing yielded crude product which was further purified by distillation through a ten-plate perforated column to provide the product ether (boiling range 82–84° C.; 96.2% purity by GLC). The product identity was confirmed by GCMS and by $^1$H and $^{19}$F NMR.

Preparation of $C_5F_{11}OC_2H_5$

The title compound was prepared essentially as in Example 3 using anhydrous potassium fluoride (38.6 g, 0.67 mol), anhydrous diethylene glycol dimethyl ether (diglyme, 500 g), methyltrialkyl ($C_8$–$C_{10}$) ammonium chloride (Adogen™ 464, available from Aldrich Chemical Company, 10.5 g), $C_4F_9COF$ (260 g of 60.7% purity, 0.59 mol), and diethyl sulfate (102.4 g, 0.67 mol). The reaction mixture was stirred at room temperature overnight, and then the resulting product was azeotropically distilled from the reaction mixture. The lower product phase of the resulting distillate was separated from the upper phase and was treated with approximately 50 g of 50% aqueous potassium hydroxide, was refluxed for four hours, and was stirred at room temperature overnight. A second azeotropic distillation and water washing gave crude product which was further purified by distillation through a ten-plate perforated column to provide the product ether (boiling point 96° C.; 99.6% purity by GLC). The product identity was confirmed by GCMS and by $^1$H and $^{19}$F NMR.

Solvency Properties

A number of potential solvents were tested for their ability to dissolve hydrocarbons of increasing molecular weight according to the procedure described in U.S. Pat. No. 5,275,669 (Van Der Puy et al.), the description of which is incorporated herein by reference. The data shown in Table 1 were obtained by determining the largest normal hydrocarbon alkane which was soluble in a particular solvent at a level of 50 percent by volume. The numbers in the Table correspond with the carbon number of the largest alkane, e.g., "8" refers to octane. Measurements were made from room temperature up to the boiling point of the solvent. For comparative purposes, hydrofluorocarbons (HFCs) and perfluorocarbons (PFCs) were also tested using this method.

The data in Table 1 show that hydrocarbon alkanes are significantly more soluble in the alkoxy-substituted perfluorocompounds used in the cleaning process of this invention than in the comparative compounds, the HFCs and PFCs. This improved solvency was more pronounced at elevated temperatures. Thus, the cleaning process of the invention can be used to remove higher molecular weight hydrocarbons (e.g., oils and greases) from substrate surfaces than can be removed using HFCs or PFCs. The higher solvency of the alkoxy-substituted perfluorocompounds for hydrocarbon alkanes indicates that these perfluorocompounds can serve not only as superior cleaning solvents for removing hydrocarbon soils, but can also be effective as solvents for depositing hydrocarbon coatings, e.g., coatings of lubricant, onto substrate surfaces.

Using essentially the above-described method, the solvency properties of other alkoxy-substituted perfluorocompounds were tested at room temperature. The compounds tested and the results obtained are shown in Table 2 below.

TABLE 2

| Compound | Largest Soluble |
|---|---|
| perfluorocyclohexyl-$CF_2OCH_3$ | 9 |
| perfluorocyclohexyl-$CF_2OC_2H_5$ | 11 |
| $C_6F_{17}OCH_3$ | 6 |
| $(CF_3)_2CFCF_2OCH_3$ | 9 |
| $C_2F_5CF(OCH_3)CF(CF_3)_2$ | 8 |
| $CF_3CF(OCH_3)CF(CF_3)_2$ | 9 |
| $C_3F_7OCH_3$ | 10 |
| $C_5F_{11}OCH_3$ | 8 |
| $C_5F_{11}OC_2H_5$ | 10 |
| $CF_3$-perfluorocyclohexyl-$CF_2OCH_3$ | 8 |
| perfluorocyclohexyl-$N(CF_2)_3OCH_3$ | 7 |
| perfluorocyclohexyl-$N(CF_2)_2OCH_3$ | 9 |

TABLE 1

| Temperature (° C.) | $C_4F_9OCH_3$ | $C_4F_9OC_2H_5$ | c-$C_6F_{11}OCH_3$ | $CF_3CFHCFHC_2F_5$ | $C_6F_{14}$ | $C_8F_{18}$ | $C_5F_{11}H$ | $C_6F_{13}H$ |
|---|---|---|---|---|---|---|---|---|
| 23 | 9 | 12 | 10 | 7 | 6 | 5 | 7 | 7 |
| 30 | 10 | 12 | 11 | 7 | | | | |
| 40 | 10 | 13 | 11 | 8 | 6 | 6 | 8 | 8 |
| 50 | 12 | 14 | 13 | 8 | 7 | 6 | | 8 |
| 55 | 12 | 15 | 13 | 9 | | | | |
| 60 | 12 | 15 | 13 | | 7 | 7 | | 9 |
| 73 | | 17 | 15 | | | 7 | | 10 |
| 101 | | 18 | | | | 9 | | |

TABLE 2-continued

| Compound | Largest Soluble |
|---|---|
|  | 8 |

Examples 8–10 and Comparative Examples A–C

In the following Examples and Comparative Examples, the cleaning ability of the alkoxy-substituted perfluorocompounds used in the cleaning process of the invention was further evaluated. A 1.28 cm×1.28 cm×0.225 cm wire-wrapped, aluminum coupon was coated with white heavy mineral oil (available from Aldrich Chemical) by immersing the coupon in an oil-filled beaker. The initial amount of the oil on the coupon was determined by weighing it on an analytical balance to the nearest 0.1 mg. The coupon was immersed in a container of solvent and sonicated for 1 minute at the indicated temperature (see Table 3 below for the solvents and temperatures used). The coupon was then weighed again, and the results were recorded in Table 3 as percent oil removal.

TABLE 3

| Example Temp. (° C.) | 8 $C_4F_9OCH_3$ | 9 $C_4F_9OC_2H_5$ | 10 c—$C_6F_{11}OCH_3$ | Comparative A $C_6F_{14}$ | Comparative B $C_6F_{13}H$ | Comparative C $CF_2ClCFCl_2$ |
|---|---|---|---|---|---|---|
| 23 | 60.3 | 56.0 | 74.4 | 54.9 | 71.7 | 98.9 |
| 50 | 98.7 | 99.2 | 96.5 | 67.6 | 86.8 | 98.7 |
| 60 | 99.9 | 100.0 | 99.8 | | | |

The data in Table 3 show that the alkoxy-substituted perfluorocompounds removed amounts of the mineral oil which were comparable to the amounts removed by the comparative PFC and HFC compounds at room temperature. At elevated temperature, the cleaning properties of the perfluorocompounds were superior to those of the PFC and HFC compounds and equivalent to those of the comparative CFC compound.

Examples 11–13

Using essentially the same procedure as that described in Examples 8–10, the ability of the alkoxy-substituted perfluorocompounds to remove a fluorinated oil was evaluated. As in the previous Examples, a coupon was immersed in Krytox™ 157FSM perfluoropolyether oil having carboxylic acid end groups (available from DuPont), and the percent oil remaining after immersion in the solvent (at room temperature) was determined. The results are shown in Table 4 below.

TABLE 4

| Example | 11 | 12 | 13 |
|---|---|---|---|
| Compound | $C_4F_9OCH_3$ | $C_4F_9OC_2H_5$ | c—$C_6F_{11}OCH_3$ |
| % Removed | 99.1 | 99.3 | 96.5 |

The data show that the alkoxy-substituted perfluorocompounds very effectively removed the perfluoropolyether oil from the surface of the coupon. This indicates that the perfluorocompounds can function well as cleaning solvents for the removal of halogenated compounds such as halogenated oils and greases.

Examples 14–16 and Comparative Examples D–E

The ability of alkoxy-substituted perfluorocompounds to function as a rinse agent in a co-solvent cleaning process was evaluated. The above-described aluminum coupon was coated with solder flux (available from Alpha Metals as Alpha 611 rosin, mildly activated flux) by immersing the coupon into a flux-filled beaker. The flux-coated coupon was then dried using a forced air convection drier. The initial amount of the flux on the coupon was determined by weighing it on an analytical balance to the nearest 0.1 mg. The coupon was immersed in a container of a mixed solvating agent comprising approximately 50% methyl decanoate and 50% dipropylene glycol di-n-butyl ether and was sonicated for 1 minute at approximately 55° C. The coupon was then immersed for 30 seconds into alkoxy-substituted perfluorocompound which had been heated to its boiling point. The coupon was weighed again, and the results were recorded in Table 5 below as percent oil removed from the coupon.

TABLE 5

| Example | 14 | 15 | 16 | Comparative D | Comparative E |
|---|---|---|---|---|---|
| Compound % Removed | $C_4F_9OCH_3$ 100.0 | $C_4F_9OC_2H_5$ 100.0 | c—$C_6F_{11}OCH_3$ 100.0 | $C_6F_{14}$ 51.9 | $C_6F_{13}H$ 91.2 |

The data in Table 5 show that the alkoxy-substituted perfluorocompounds (used according to the cleaning process of the invention) effectively removed the solvating agent and flux residues, showing solvency properties superior to those of the comparative PFC and HFC compounds.

Examples 17–18 and Comparative Example F

The above-described aluminum coupon was dipped into Brayco 815Z perfluoropolyether oil (available from Castrol Inc., molecular weight of about 10,000) and then immersed in alkoxy-substituted perfluorocompound vapor (over the boiling liquid) for 60 seconds. The percent oil removal was determined in the above-described manner. The results are shown in Table 6.

TABLE 6

|  | 17 | 18 | Comparative F |
|---|---|---|---|
| Compound | $C_4F_9OCH_3$ | $C_4F_9OC_2H_5$ | $C_6F_{14}$ |
| Percent Soil Removed | 89.9% | 93.3% | 92.9% |

Examples 19–20 and Comparative Example G

The above-described test coupon was dipped into a paraffinic oil comprising a mixture of linear and branched hydrocarbons (DuoSeal Pump Oil, available from Sargent Welch), was immersed in mixed solvating agent comprising approximately 50% methyl caproate and 50% dipropylene glycol di-n-butyl ether for 30 seconds, and was then rinsed in boiling alkoxy-substituted perfluorocompound for 30 seconds. The percent oil removal was determined in the above-described manner. The results are shown in Table 7.

TABLE 7

|  | 19 | 20 | Comparative G |
|---|---|---|---|
| Compound | $C_4F_9OCH_3$ | $C_4F_9OC_2H_5$ | $C_6F_{14}$ |
| Percent Soil Removed | 99.8% | 100.0% | 89.2% |

Examples 21–22

The above-described test coupon was dipped in white heavy mineral oil (available from Aldrich Chemical), was immersed in a boiling single-phase mixture of 40 volume % of a solvating agent comprising essentially methyl decanoate and 60 volume % of alkoxy-substituted perfluorocompound (a cleaning composition of the invention) for 60 seconds, was cooled for 60 seconds, and was then immersed in mixture vapor for 30 seconds. The percent oil removal was determined in the above-described manner. The results are shown in Table 8.

TABLE 8

|  | 21 | 22 |
|---|---|---|
| Fluorinated Component of Cleaning Composition | $C_4F_9OCH_3$ | $C_4F_9OC_2H_5$ |
| Percent Soil Removed | 94.61% | 94.28% |

Examples 23–24 and Comparative Example H

The above-described test coupon was dipped into Duo-Seal Pump Oil (available from Sargent-Welch), was immersed in a boiling mixture of 40 volume % of a solvating agent comprising mixed terpenes having a boiling range of 243–274° C. and 60 volume % of alkoxy-substituted perfluorocompound (a cleaning composition of the invention), was cooled for 60 seconds, and was then immersed in mixture vapor for 30 seconds. The percent oil removal was determined in the above-described manner. The results are shown in Table 9.

TABLE 9

|  | 23 | 24 | Comparative H |
|---|---|---|---|
| Fluorinated Component of Cleaning Composition | $C_4F_9OCH_3$ | $C_4F_9OC_2H_5$ | $C_6F_{14}$ |
| Percent Soil Removed | 86.4% | 99.4% | 75.7% |

Examples 25–26 and Comparative Example I

The above-described test coupon was dipped into Duo-Seal Pump Oil (available from Sargent-Welch) and was then immersed in a mixture of 40 volume % n-$C_6H_{14}$ and 60 volume % alkoxy-substituted perfluorocompound (a cleaning composition of the invention) for 60 seconds at room temperature with ultrasonic agitation. The percent oil removal was determined in the above-described manner. The results are shown in Table 10.

TABLE 10

|  | 25 | 26 | Comparative I |
|---|---|---|---|
| Fluorinated Component of Cleaning Composition | $C_4F_9OCH_3$ | $C_4F_9OC_2H_5$ | $C_6F_{14}$ |
| Percent Soil Removed | 92.5% | 99.0% | 88.5% |

Examples 27–28 and Comparative Example J

The above-described test coupon was dipped into Duo-Seal Pump Oil (available from Sargent-Welch) and was then immersed in the vapor of a boiling mixture of 40 volume % n-$C_6H_{14}$ and 60 volume % alkoxy-substituted perfluorocompound (a cleaning composition of the invention) for 60 seconds. The percent oil removal was determined in the above-described manner. The results are shown in Table 11.

TABLE 11

| Example | 27 | 28 | Comparative J |
|---|---|---|---|
| Fluorinated Component of Cleaning Composition | $C_4F_9OCH_3$ | $C_4F_9OC_2H_5$ | $C_6F_{14}$ |
| Percent Soil Removed | 90.8% | 97.1% | 73.8% |

The results obtained in Examples 17–28 show that alkoxy-substituted perfluorocompounds are effective at removing a variety of contaminants from substrate surfaces.

Examples 29–38 describe the preparation of coating compositions of the invention and the evaluation of alkoxy-substituted perfluorocompounds for use according to the coating process of the invention.

Examples 29–31

The ability of alkoxy-substituted perfluorocompounds to dissolve several halogenated oils was determined by adding a measured amount of oil to alkoxy-substituted perfluorocompound until the resulting mixture became turbid or phase-split. Miscibility was defined as greater than or equal to 50 percent by volume solubility at room temperature. The results (shown in Table 12) indicate that alkoxy-substituted perfluorocompounds have very high ability to dissolve halogenated oils. Thus, the perfluorocompounds can be used as carrier solvents for halogenated oils in the deposition of coatings of such oils on substrate surfaces.

TABLE 12

| Example Compound Solute | 29 $C_4F_9OCH_3$ | 30 $C_4F_9OC_2H_5$ | 31 c—$C_6F_{11}OCH_3$ |
|---|---|---|---|
| Brayco 815Z perfluoropolyether (MW about 10,000) | Miscible | Miscible | Miscible |
| Fomblin ™ AM-2001 Functionalized perfluoropolyether (available from Ausimont Inc.) | Miscible | Miscible | Miscible |
| Chlorotrifluoroethylene Fluid (available from Inland as Inland 41 Vacuum Pump Oil) | Miscible | Miscible | Miscible |

Examples 32–38 and Comparative Examples K–L

To demonstrate the use of alkoxy-substituted perfluorocompounds as dispersing agents, a series of polytetrafluoroethylene (PTFE) dispersions were prepared and evaluated. Commercially, PTFE is available from DuPont as Teflon™ powder or as Vydax™ dispersions in either water or isopropanol (IPA) (20–30 weight %). To prepare useful coatings, these concentrated dispersions must be further diluted with a co-dispersant to 1–10 weight %, more frequently 1–3 weight %. Although the commercial PTFE dispersions may be further diluted with either water or isopropanol, these fluids are often not-preferred due to performance and/or safety reasons.

In the following Examples 32–38, the commercially-available, concentrated dispersions were diluted at room temperature with alkoxy-substituted perfluorocompound or with a comparative compound (perfluoro-N-methyl morpholine) to produce a dilute dispersion of approximately 1.5 weight %. The resulting dispersions were then evaluated as to homogeneity and assigned one of the ratings shown in Table 13 below. A description of the dispersions prepared and the results obtained are shown in Table 14.

TABLE 13

| Rating | Rating Description |
|---|---|
| Poor | Agglomerated PTFE--not useful. |
| Fair | Some agglomeration; extensive grainy or waxy coating on the surface of glass vial. |
| Good | Homogeneous dispersion; some grainy coating on glass vial. |
| Very Good | Homogeneous dispersion; little to no grainy coating on glass vial. |

TABLE 14

| Example No. | Product | Dispersant | Final Dispersion Weight % | Rating |
|---|---|---|---|---|
| 32 | Vydax ™ AR/IPA | $C_4F_9OCH_3$ | 1.49 | Very Good |
| 33 | Vydax ™ HD/IPA | $C_4F_9OCH_3$ | 1.52 | Very Good |
| 34 | Teflon ™ MP1100/IPA | $C_4F_9OCH_3$ | 1.59 | Very Good |
| 35 | Teflon ™ MP1100/IPA | $C_4F_9OCH_2CH_3$ | 1.52 | Very Good |
| 36 | Vydax ™ ARW/Water | $C_4F_9OCH_3$ | 0.92 | Fair to Good |
| 37 | Vydax ™ ARW/Water | $C_4F_9OCH_2CH_3$ | 0.91 | Fair to Good |
| 38 | Vydax ™ ARW/Water | $C_4F_9OCH_2CH_3$ | 1.49 | Fair to Good |
| Comparative K | Vydax ™ AR/IPA | Perfluoro-N-methyl morpholine | 1.50 | Poor |
| Comparative L | Vydax ™ ARW/Water | Perfluoro-N-methyl morpholine | 1.50 | Poor |

The data show that alkoxy-substituted perfluorocompounds can be used to prepare homogeneous dispersions of PTFE, whereas the comparative PFC compound cannot. Thus, the perfluorocompounds can be used as carrier solvents for PTFE in the deposition of coatings of PTFE on substrate surfaces.

Examples 39–44 describe the use of alkoxy-substituted perfluorocompounds in water removal (drying) according to the cleaning process of the invention.

Examples 39–44

A series of water displacement compositions was prepared and evaluated. The compositions comprised alkoxy-substituted perfluorocompound and either a surface active agent ($C_4F_9OC_2F_4OCF_2CONHC_2H_4OH$, described in U.S. Pat. Nos. 5,125,978 and 5,089,152 (Flynn et al.)) or a co-solvent. The compositions (and the results obtained) are shown in Table 15 below.

The following procedure was utilized; an 11.7 mm O.D. by 32 mm glass vial was wetted with deionized water. The wetted vial was placed in a vessel containing a water displacement composition which had been heated to its boiling point. A saturated zone of alkoxy-substituted perfluorocompound (and cosolvent, if any) vapor was maintained above the boiling composition. The vial was agitated by ultrasound for 1 minute while dislodging and displacing any adhering water. The vial was then removed from the boiling composition and held in the saturated vapor zone for 30–60 seconds to allow drainage of excess water displacement composition back into the vessel and thereby minimize fluid carryout. The vial was then visually inspected for the presence of residual water. The results are shown in Table 15 below, where a "+" indicates that 75% of the water was removed from the vial in 60 seconds.

TABLE 15

| Ex. No. | Alkoxy-substituted Perfluorocompound | Co-solvent (5 Volume %) | Concentration of Surface Active Agent (weight %) | Water Removal |
|---|---|---|---|---|
| 39 | $C_4F_9OCH_3$ | None | 0.2 | + |
| 40 | $C_4F_9OC_2H_5$ | None | 0.2 | + |
| 41 | $C_4F_9OCH_3$ | $CH_3OH$ | None | + |
| 42 | $C_4F_9OCH_3$ | $(CH_3)_2CHOH$ | None | + |
| 43 | $C_4F_9OC_2H_5$ | $CH_3OH$ | None | + |
| 44 | $C_4F_9C_2H_5$ | $(CH_3)_2CHOH$ | None | + |

The results in Table 15 show that alkoxy-substituted perfluorocompounds are effective in removing water from substrate surfaces.

In Examples 45–65 and Comparative Examples M–Z and A'–G', the properties of an alkoxy-substituted perfluorocompound used in the process and composition of this invention, perfluorobutyl methyl ether ($C_4F_9OCH_3$), were compared with the properties of 2-chloro-1,1,2-trifluoroethyl methyl ether ($CHClFCF_2OCH_3$), described in U.S. Pat. No. 3,278,615 (Larsen et al.). Comparisons were made for both the neat ether compounds and blends thereof with co-solvent.

Examples 45–65 and Comparative Examples M–Z and A'–G'

Various properties were measured for $C_4F_9OCH_3$, $CHClFCF_2OCH_3$, and blends of each ether compound with co-solvent, trans-1,2-dichloroethylene (hereinafter, t-DCE) or n-butyl bromide, at various weight ratios. The results of these measurements are shown in Tables 16 and 17 below.

TABLE 16

| Test | Weight % Ether | Weight % t-DCE | Ex. No. | Test Data for $C_4F_9OCH_3$ (Example) | Test Data for $CHClFCF_2OCH_3$ (Comp. Ex.) | Comparative Ex. No. |
|---|---|---|---|---|---|---|
| Open Cup Flash Point (ASTM D1310-86), ° F. (° C.) | 100 | 0 | 45 | none | 76 (24) | M |
| | 80 | 20 | 46 | none | 85 (29) | N |
| | 50 | 50 | 47 | none | 80 (27) | O |
| | 20 | 80 | 48 | none | 80 (27) | P |
| Largest Carbon Number of Longest Hydrocarbon Alkane to Dissolve[1] | 100 | 0 | 49 | 9 | 18 | Q |
| | 80 | 20 | 50 | 11 | 19 | R |
| | 50 | 50 | 51 | 16 | 21 | S |
| | 20 | 80 | 52 | 22 | 27 | T |

[1]Determined as described above in "Solvency Properties" section.

TABLE 17

| Test | Weight % Ether | Weight % n-Butyl Bromide | Ex. No. | Test Data for $C_4F_9OCH_3$ (Example) | Test Data for $CHClFCF_2OCH_3$ (Comp. Ex.) | Comparative Ex. No. |
|---|---|---|---|---|---|---|
| Closed Cup Flash Point (ASTM D3278-96), ° F. (° C) | 100 | 0 | 53 | none[4] | 45 (7) | U |
| | 80 | 20 | 54 | none[4] | 50 (10) | V |
| | 50 | 50 | 55 | none[4] | 45 (7) | W |
| | 30 | 70 | 56 | none[4] | 45 (10) | X |
| | 20 | 80 | 57 | none[4] | 50 (7) | Y |
| Atmospheric Lifetime (years)[1] | 100 | 0 | 58 | 4.1 | 0.27 | Z |
| Ozone Depletion Potential (ODP) (CFC-11 = 1) | 100 | 0 | 59 | none[5] | 0.0015[6] | A' |
| Largest Carbon Number of Longest Hydrocarbon Alkane to Dissolve[2] | 100 | 0 | 60 | 9 | 18 | B' |
| | 80 | 20 | 61 | 11 | 19 | C' |
| | 50 | 50 | 62 | 15 | 20 | D' |
| | 30 | 70 | 63 | 21 | 21 | E' |
| | 20 | 80 | 64 | 21 | 21 | F' |
| Stability in Presence of Acid[3] | 100 | 0 | 65 | no rxn. (0% con-version to ester) | quantita-tive (100% conversion to ester) | G' |

[1]Determined as described above in "Atmospheric Lifetime" section, except based upon an updated value of 8.9 years for the atmospheric lifetime of methane, as reported by R. G. Prinn et al. in Science, Volume 269, July 14, 1995, pages 187–192.
[2]Determined as described above in "Solvency Properties" section.
[3]Determined as described above in "Stability in the Presence of Acid" section.
[4]During testing, the temperature of the closed cup flash point apparatus was gradually raised to 140° F. (60° C.). This upper temperature was close to the boiling point for the $C_4F_9OCH_3$ mixtures.
[5]Compounds containing fluorine as the only halogen have been shown to have no impact on stratospheric ozone, as described by A. R. Ravishankara et al. in Science, Volume 263, January 7, 1994, pages 71–75 and by J. S. Francisco and M. M. Maricq in Accounts in Chemical Research 29, 391–397 (1996)
[6]The estimated value for $CHClFCF_2OCH_3$ was based on HCFC123, which has an ODP of 0.012.

The data in Tables 16 and 17 shows that the alkoxy-substituted perfluorocompound and blends thereof used in the process and composition of this invention exhibit significantly different properties from those of the ether compound of U.S. Pat. No. 3,278,615 (hereinafter, the '615 compound) and corresponding blends. For example, unlike the '615 compound, the alkoxy-substituted perfluorocompound does not deplete stratospheric ozone and is not flammable. The alkoxy-substituted perfluorocompound exhibits superior chemical stability to that of the '615 compound (that is, the perfluorocompound does not hydrolyze in the presence of acids, whereas the '615 compound is quantitatively converted to ester). Finally, and most surprisingly, unlike the '615 compound, the alkoxy-substituted perfluorocompound does not form flammable mixtures or blends (over a wide range of weight ratios) with flammable co-solvents such as trans-1,2-dichloroethylene and n-butyl bromide. Such blends of perfluorocompound and flammable co-solvent can thus surprisingly be used for cleaning where desired.

Various modifications and alterations of this invention will become apparent to those skilled in the art without departing from the scope and spirit of this invention.

We claim:

1. A cleaning composition comprising (a) at least one mono-, di-, or trialkoxy-substituted perfluoroalkane, perfluorocycloalkane, perfluorocycloalkyl-containing perfluoroalkane, or perfluorocycloalkylene-containing perfluoroalkane compound, said compound optionally containing one or more additional catenary heteroatoms; and (b) at least one surface active agent.

2. The cleaning composition according to claim 1 wherein said surface active agent is a non-ionic fluoroaliphatic surface active agent.

* * * * *

UNITED STATES PATENT AND TRADEMARK OFFICE
CERTIFICATE OF CORRECTION

PATENT NO. : 6,509,309 B2
DATED : January 21, 2003
INVENTOR(S) : Flynn, Richard M.

It is certified that error appears in the above-identified patent and that said Letters Patent is hereby corrected as shown below:

Column 9,
Line 54, delete "Water-free" and insert in place thereof -- water-free --

Column 14,
Line 51, delete "$F^{31}$" and insert in place thereof -- $F^-$ --

Column 22,
Line 30, delete "$CF_2OC_2H_3$" and insert in place thereof -- $CF_2OC_2H_5$ --
Line 32, delete "$C_6F_{17}OCH_{13}$" and insert in place thereof -- $C_8F_{17}OCH_{13}$ --

Signed and Sealed this

Eighteenth Day of May, 2004

JON W. DUDAS
*Acting Director of the United States Patent and Trademark Office*